(12) United States Patent
Vendely et al.

(10) Patent No.: US 11,039,832 B2
(45) Date of Patent: Jun. 22, 2021

(54) SURGICAL STAPLER BUTTRESS APPLICATOR WITH SPENT STAPLE CARTRIDGE LOCKOUT

(71) Applicant: Ethicon Endo-Surgery, LLC, Guaynabo, PR (US)

(72) Inventors: Michael J. Vendely, Lebanon, OH (US); Jason L Harris, Lebanon, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 1054 days.

(21) Appl. No.: 14/926,322

(22) Filed: Oct. 29, 2015

(65) Prior Publication Data

US 2017/0055980 A1  Mar. 2, 2017

Related U.S. Application Data

(60) Provisional application No. 62/209,041, filed on Aug. 24, 2015.

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07207* (2013.01); *A61B 17/07292* (2013.01);
(Continued)

(58) Field of Classification Search
CPC .................................. A61B 50/30; A61B 90/03
(Continued)

(56) References Cited

U.S. PATENT DOCUMENTS

| 4,805,823 A | 2/1989 | Rothfuss |
| 5,415,334 A | 5/1995 | Williamson et al. |

(Continued)

FOREIGN PATENT DOCUMENTS

| CN | 101366647 A | 2/2009 |
| CN | 201806743 U | 4/2011 |

(Continued)

OTHER PUBLICATIONS

U.S. Appl. No. 14/926,764.
(Continued)

*Primary Examiner* — Anna K Kinsaul
*Assistant Examiner* — Daniel Jeremy Leeds
(74) *Attorney, Agent, or Firm* — Frost Brown Todd LLC

(57) ABSTRACT

An apparatus includes a housing, a platform, a buttress assembly and a lockout feature. The housing defines a gap that is configured to receive a portion of an end effector of a surgical stapler. A portion of the platform is exposed in the gap defined by the housing. The buttress assembly is positioned on the platform. The buttress assembly is exposed in the gap defined by the housing. The lockout feature is configured to enable an end effector with an unspent staple cartridge to clamp onto the platform and thereby engage the first buttress assembly. The lockout feature is further configured to prevent an end effector with a spent staple cartridge from clamping onto the platform to thereby engage the first buttress assembly.

20 Claims, 10 Drawing Sheets

(51) Int. Cl.
   *A61B 50/30* (2016.01)
   *A61B 17/10* (2006.01)
   *A61B 90/00* (2016.01)
   *A61B 50/00* (2016.01)
   *A61B 17/00* (2006.01)
   *A61B 17/29* (2006.01)

(52) U.S. Cl.
   CPC ............ *A61B 17/105* (2013.01); *A61B 50/30* (2016.02); *A61B 2017/0053* (2013.01); *A61B 2017/07271* (2013.01); *A61B 2017/2927* (2013.01); *A61B 2050/005* (2016.02); *A61B 2050/0059* (2016.02); *A61B 2090/081* (2016.02); *A61B 2090/0811* (2016.02); *A61B 2090/0814* (2016.02)

(58) Field of Classification Search
   USPC ...... 227/175.1, 176.1, 179.1, 180.1; 606/139
   See application file for complete search history.

(56) References Cited

U.S. PATENT DOCUMENTS

| | | |
|---|---|---|
| 5,441,191 A | 8/1995 | Linden |
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,752,965 A * | 5/1998 | Francis ............ A61B 17/07207 227/178.1 |
| 5,792,135 A | 8/1998 | Madhani et al. |
| 5,814,055 A | 9/1998 | Knodel et al. |
| 5,817,084 A | 10/1998 | Jensen |
| 5,878,193 A | 3/1999 | Wang et al. |
| 6,231,565 B1 | 5/2001 | Tovey et al. |
| 6,273,897 B1 | 8/2001 | Dalessandro et al. |
| 6,364,888 B1 | 4/2002 | Niemeyer et al. |
| 6,783,524 B2 | 8/2004 | Anderson et al. |
| 6,939,358 B2 | 9/2005 | Palacios et al. |
| 6,978,921 B2 | 12/2005 | Shelton, IV et al. |
| 6,988,649 B2 * | 1/2006 | Shelton, IV ..... A61B 17/07207 227/175.2 |
| 7,000,818 B2 | 2/2006 | Shelton, IV et al. |
| 7,143,923 B2 | 12/2006 | Shelton, IV et al. |
| 7,303,108 B2 | 12/2007 | Shelton, IV |
| 7,367,485 B2 | 5/2008 | Shelton, IV et al. |
| 7,380,695 B2 * | 6/2008 | Doll ................ A61B 17/07207 227/175.1 |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,524,320 B2 | 4/2009 | Tierney |
| 7,691,098 B2 | 4/2010 | Wallace |
| 7,721,930 B2 | 5/2010 | McKenna et al. |
| 7,806,891 B2 | 10/2010 | Nowlin et al. |
| 8,141,762 B2 | 3/2012 | Bedi et al. |
| 8,210,032 B2 * | 7/2012 | Sanford ............... G01N 31/222 73/29.02 |
| 8,210,411 B2 | 7/2012 | Yates et al. |
| 8,371,491 B2 | 2/2013 | Huitema et al. |
| 8,408,439 B2 | 4/2013 | Huang et al. |
| 8,453,914 B2 | 6/2013 | Laurent et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,616,431 B2 | 12/2013 | Timm et al. |
| 8,783,541 B2 | 7/2014 | Shelton, IV et al. |
| 8,800,838 B2 | 8/2014 | Shelton, IV |
| 8,801,735 B2 | 8/2014 | Shelton, IV et al. |
| 8,814,025 B2 | 8/2014 | Miller et al. |
| 8,820,605 B2 | 9/2014 | Shelton, IV |
| 8,844,789 B2 | 9/2014 | Shelton, IV et al. |
| 8,899,464 B2 | 12/2014 | Hueil et al. |
| 8,998,060 B2 | 4/2015 | Bruewer et al. |
| 9,060,770 B2 | 6/2015 | Shelton, IV et al. |
| 9,101,359 B2 | 8/2015 | Smith et al. |
| 9,186,142 B2 | 11/2015 | Fanelli et al. |
| 9,198,644 B2 | 12/2015 | Balek et al. |
| 9,198,662 B2 | 12/2015 | Barton et al. |
| 9,211,120 B2 | 12/2015 | Scheib et al. |
| 9,220,501 B2 | 12/2015 | Baxter, III et al. |
| 9,282,962 B2 | 3/2016 | Schmid et al. |
| 9,301,759 B2 | 4/2016 | Spivey et al. |
| 9,307,965 B2 | 4/2016 | Ming et al. |
| 9,364,233 B2 | 6/2016 | Alexander, III et al. |
| 9,393,018 B2 | 7/2016 | Wang et al. |
| 9,398,911 B2 | 7/2016 | Auld |
| 9,445,808 B2 | 9/2016 | Woodard et al. |
| 9,492,170 B2 | 11/2016 | Bear et al. |
| 9,517,065 B2 | 12/2016 | Simms et al. |
| 9,629,626 B2 | 4/2017 | Soltz et al. |
| 9,770,245 B2 | 9/2017 | Swayze et al. |
| 10,052,105 B2 | 8/2018 | Tannhauser et al. |
| 10,166,023 B2 | 1/2019 | Vendely et al. |
| 10,342,532 B2 | 7/2019 | Zeiner et al. |
| 10,345,542 B2 | 7/2019 | Vendely et al. |
| 10,349,940 B2 | 7/2019 | Vendely et al. |
| 2003/0120284 A1 * | 6/2003 | Palacios ............ A61B 17/07207 606/139 |
| 2004/0232199 A1 * | 11/2004 | Shelton, IV ..... A61B 17/07207 227/175.2 |
| 2005/0070929 A1 * | 3/2005 | Dalessandro .... A61B 17/07207 606/151 |
| 2006/0173470 A1 | 8/2006 | Oray et al. |
| 2008/0169328 A1 | 7/2008 | Shelton, IV |
| 2009/0095791 A1 * | 4/2009 | Eskaros ............... A61B 17/072 227/175.1 |
| 2009/0205986 A1 | 8/2009 | Baker et al. |
| 2009/0206126 A1 | 8/2009 | Huitema et al. |
| 2009/0206131 A1 | 8/2009 | Weisenburgh, II et al. |
| 2009/0206142 A1 * | 8/2009 | Huitema .......... A61B 17/07207 227/176.1 |
| 2009/0273480 A1 * | 11/2009 | Mittleman .......... H04M 1/0274 340/604 |
| 2010/0234861 A1 | 9/2010 | Oray et al. |
| 2011/0290856 A1 | 12/2011 | Shelton, IV et al. |
| 2012/0241492 A1 | 9/2012 | Shelton, IV et al. |
| 2012/0241493 A1 | 9/2012 | Baxter, III et al. |
| 2012/0241499 A1 * | 9/2012 | Baxter, III ........... A61B 17/072 227/176.1 |
| 2012/0289979 A1 * | 11/2012 | Eskaros ............ A61B 17/07292 606/151 |
| 2012/0292367 A1 | 11/2012 | Morgan et al. |
| 2013/0062391 A1 | 3/2013 | Boudreaux et al. |
| 2013/0068816 A1 | 3/2013 | Vasudevan et al. |
| 2013/0075447 A1 | 3/2013 | Weisenburgh, II et al. |
| 2013/0206813 A1 | 8/2013 | Nalagatla |
| 2013/0214030 A1 | 8/2013 | Aronhalt et al. |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0263563 A1 | 9/2014 | Stokes et al. |
| 2015/0076212 A1 | 3/2015 | Shelton, IV et al. |
| 2015/0272575 A1 | 10/2015 | Leimbach et al. |
| 2015/0351754 A1 | 12/2015 | Harris et al. |
| 2015/0351758 A1 | 12/2015 | Shelton, IV et al. |
| 2015/0351763 A1 | 12/2015 | Shelton, IV et al. |
| 2015/0374360 A1 | 12/2015 | Scheib et al. |
| 2015/0374373 A1 | 12/2015 | Rector et al. |
| 2016/0089142 A1 | 3/2016 | Harris et al. |
| 2016/0089146 A1 | 3/2016 | Harris et al. |
| 2016/0278774 A1 | 9/2016 | Shelton, IV et al. |
| 2017/0027567 A1 | 2/2017 | Scheib et al. |
| 2017/0027568 A1 | 2/2017 | Scheib et al. |
| 2017/0027569 A1 | 2/2017 | Scheib et al. |
| 2017/0049444 A1 | 2/2017 | Schellin et al. |

(56) References Cited

U.S. PATENT DOCUMENTS

| | | |
|---|---|---|
| 2017/0055981 A1 | 3/2017 | Vendely et al. |
| 2017/0055982 A1 | 3/2017 | Zeiner et al. |
| 2017/0055986 A1 | 3/2017 | Harris et al. |
| 2017/0056016 A1 | 3/2017 | Barton et al. |
| 2017/0056017 A1 | 3/2017 | Vendely et al. |
| 2017/0056018 A1 | 3/2017 | Zeiner et al. |

FOREIGN PATENT DOCUMENTS

| | | |
|---|---|---|
| CN | 102307531 A | 1/2012 |
| CN | 203195731 U | 9/2013 |
| CN | 103957818 A | 7/2014 |
| CN | 103961149 A | 8/2014 |
| CN | 104224286 A | 12/2014 |
| CN | 104321023 A | 1/2015 |
| CN | 104 379 068 A | 2/2015 |
| CN | 104411255 A | 3/2015 |
| CN | 104837416 A | 8/2015 |
| EP | 2 090 248 A2 | 9/2009 |
| EP | 16185368 A2 | 8/2014 |
| EP | 3072460 A2 | 9/2016 |
| EP | 16185370 A2 | 9/2016 |
| JP | 2001-502575 A | 2/2001 |
| JP | 2012-130729 | 7/2012 |
| JP | 2015-514471 A | 5/2015 |
| WO | WO 2005/079675 A2 | 9/2005 |
| WO | WO 2013/119365 A1 | 8/2013 |

OTHER PUBLICATIONS

Extended European Search Report and Written Opinion dated Jan. 20, 2017 for Application No. EP 16185368.4, 10 pgs. Extended European Search Report and Written Opinion dated Jan. 24, 2017 for Application No. EP 16185370.0, 11 pgs. Extended European Search Report and Written Opinion dated Jun. 8, 2017 for Application No. EP 16185375.9, 16 pgs.
Extended European Search Report and Written Opinion dated Jan. 24, 2017 for Application No. EP 16185370.0, 11 pgs.
Extended European Search Report and Written Opinion dated Jun. 8, 2017 for Application No. EP 16185375.9, 16 pgs.
European Search Report and Written Opinion dated Jan. 30, 2017 for Application No. EP 16185376.7, 14 pgs.
European Search Report and Written Opinion dated Jan. 24, 2017 for Application No. EP 16185387.4, 10 pgs.
International Search Report and Written Opinion dated Dec. 23, 2016 for Application No. PCT/US2016/048352, 16 pgs.
International Search Report and Written Opinion dated Feb. 17, 2017 for Application No. PCT/US2016/048356, 17 pgs.
International Search Report and Written Opinion dated Jan. 2, 2017 for Application No. PCT/US2016/048359, 12 pgs.
International Search Report and Written Opinion dated Dec. 21, 2016 for Application No. PCT/US2016/048362, 11 pgs.
International Search Report and Written Opinion dated Dec. 6, 2016 for Application No. PCT/US2016/048364, 12 pgs.
U.S. Appl. No. 14/871,071, filed Sep. 30, 2015.
U.S. Appl. No. 14/871,131, filed Sep. 30, 2015.
U.S. Appl. No. 14/926,027, filed Oct. 29, 2015.
U.S. Appl. No. 14/926,029, filed Oct. 29, 2015.
U.S. Appl. No. 14/926,045, filed Oct. 29, 2015.
U.S. Appl. No. 14/926,057, filed Oct. 29, 2015.
U.S. Appl. No. 14/926,072, filed Oct. 29, 2015.
U.S. Appl. No. 14/926,090, filed Oct. 29, 2015.
U.S. Appl. No. 14/926,131 filed Oct. 29, 2015.
U.S. Appl. No. 14/926,160, filed Oct. 29, 2016.
U.S. Appl. No. 14/926,194, filed Oct. 29, 2015.
U.S. Appl. No. 62/209,041, filed Aug. 24, 2015.
European Examination Report dated Jan. 3, 2018 for Application No. EP 16185368.4, 4 pgs.
European Examination Report dated Jan. 15, 2018 for Application No. EP 16185370.0, 4 pgs.
European Search Report, Extended, and Written Opinion dated Oct. 18, 2017 for Application No. EP 18182626.4, 8 pgs. European Exam Report dated Oct. 16, 2018 for Application No. EP 16185368.4, 4 pgs.
European Exam Report dated Oct. 16, 2018 for Application No. EP 16185368.4, 4 pgs.
European Communication, Decision to Grant a European Patent, dated Jan. 10, 2019 for Application No. EP 16185376.7, 2 pgs.
European Search Report, Partial, dated Jan. 25, 2017 for Application No. 16185375.9, 7 pgs.
European Communication, Decision to Grant a European Patent, dated Dec. 6, 2018 for Application No. EP 16185375.9, 2 pgs.
European Communication, Decision to Grant a European Patent, dated Jul. 4, 2019 for Applicafion No. EP 16185370.0, 2 pgs.
European Communication, Decision to Grant a European Patent, dated Aug. 30, 2018 for Application No. EP 16185387.4, 2 pgs.
U.S. Appl. No. 14/926,296.
U.S. Appl. No. 16/191,722.
U.S. Appl. No. 16/211,436.
U.S. Appl. No. 16/211,438.
U.S. Appl. No. 16/377,348.
U.S. Appl. No. 14/926,267.
U.S. Appl. No. 14/926,358.
U.S. Appl. No. 14/926,609.
U.S. Appl. No. 16/211,436; and.
U.S. Appl. No. 16/191,722, Vendely et al., filed Nov. 15, 2018.
U.S. Appl. No. 16/211,436, Vendely et al., filed Dec. 6, 2018.
U.S. Appl. No. 16/211,438, Vendely et al., filed Dec. 6, 2018.
U.S. Appl. No. 16/377,348, Vendely et al., filed Apr. 8, 2019.
U.S. Appl. No. 17/130,898; Vendely et al., filed Dec. 22, 2020.
U.S. Pat. No. 10,166,023, Vendely et al., dated Jan. 19, 2019.
U.S. Pat. No. 10,342,532, Vendely et al., dated Jul. 9, 2019.
U.S. Pat. No. 10,342,542, Vendely et al., dated Jul. 9, 2019.
U.S. Pat. No. 10,349,940, Vendely et al., dated Jul. 16, 2019.
U.S. Pat. No. 10,639,039, Vendely et al., dated May 5, 2020.
Brazilian Search Report and Written Opinion dated Jun. 5, 2020 for Appliction No. BR 112018003524-6, 4 pgs.
Brazilian Search Report and Written Opinion dated Jun. 15, 2020 for Application No. BR 112018003490-8, 4 pgs.
Brazilian Search Report and Written Opinion dated Jun. 15, 2020 for Application No. BR 12018003480-0, 4 pgs.
Brazilian Search Report and Written Opinion dated Jun. 15, 2020 for U.S. Appl. No. BR 112018003512-2, 4 pgs.
Brazilian Search Reporpt and Written Opinion dated May 5, 2020 for Application NO. BR 112018003463-0, 4 pgs.
Chinese Office Action and Search Report dated Mar. 30, 2020 for Application No. CN 2016800620957, 9 pgs.
Chinese Office Action and Search Report dated Mar. 20, 2020 for Application No. CN 20166800620887, 16 pgs.
Chinese Office Action and Search Report dated Mar. 24, 2020 for Application No. CN 201680061225.5, 16 pgs.
Chinese Office Action and Search Report dated Mar. 20, 2020 for Application No. CN 201680062109.5, 10 pgs.
Chinese Office Action and Search Report dated Mar. 20, 2020 for Application No. CN 201680061209.6, 12 pgs.
Japanese Office Action, Notification of Reasons for Refusal, dated Oct. 6, 2020 for Application No. JP 2018-510411, 4 pgs.
Japanese Office Action, Notification of Reasons for Refusal, dated May 12, 2020 for Application No. JP 2018-510440, 5 pgs.
Japanese Office Action, Notification of Reasons for Refusal, dated Jun. 30, 2020 for Application No. JP 2018-510443, 3 pgs.
Japanese Office Action, Notification of reasons for Refusal, dated Jul. 14, 2020 for Application No. JP 2018-510445, 6 pgs.
Japanese Office Action, Notification of Reasons for Refusal, dated Jun. 30, 2020 for Application No. JP 2018-510448, 3 pgs.
European Search Report and Written Opinion dated Feb. 5, 2021 for Application No. EP 20208018.0, 9 pgs.
Indian Examination Report dated Feb. 12, 2021 for Application No. Ni 201817005619, 5 pgs.

\* cited by examiner

SURGICAL STAPLER BUTTRESS APPLICATOR WITH SPENT STAPLE CARTRIDGE LOCKOUT

PRIORITY

This application claims priority to U.S. Patent App. No. 62/209,041, entitled "Method and Apparatus for Applying a Buttress to End Effector of a Surgical Stapler," filed Aug. 24, 2015, the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, issued as U.S. Pat. No. 9,597,082 on Mar. 21, 2017; U.S. Pub. No. 2014/0246473, entitled "Rotary Powered Surgical Instruments with Multiple Degrees of Freedom," published Sep. 4, 2014, issued as U.S. Pat. No. 9,398,911 on Jul. 26, 2016; U.S. Pub. No. 2013/0206813, entitled "Linear Stapler," published Aug. 15, 2013, now abandoned; U.S. Pub. No. 2008/0169328, entitled "Buttress Material for Use with a Surgical Stapler," published Jul. 17, 2008, now abandoned; U.S. patent application Ser. No. 14/300,804, entitled "Woven and Fibrous Materials for Reinforcing a Staple Line," filed Jun. 10, 2014, issued as U.S. Pat. No. 9,848,871 on Dec. 26, 2017; U.S. patent application Ser. No. 14/300,811, entitled "Devices and Methods for Sealing Staples in Tissue", issued as U.S. Pat. No. 9,936,954 on Apr. 10, 2018; and U.S. patent application Ser. No. 14/498,070, entitled "Radically Expandable Staple Line" filed Sep. 26, 2014, issued as U.S. Pat. No. 10,426,476 on Oct. 1, 2019. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
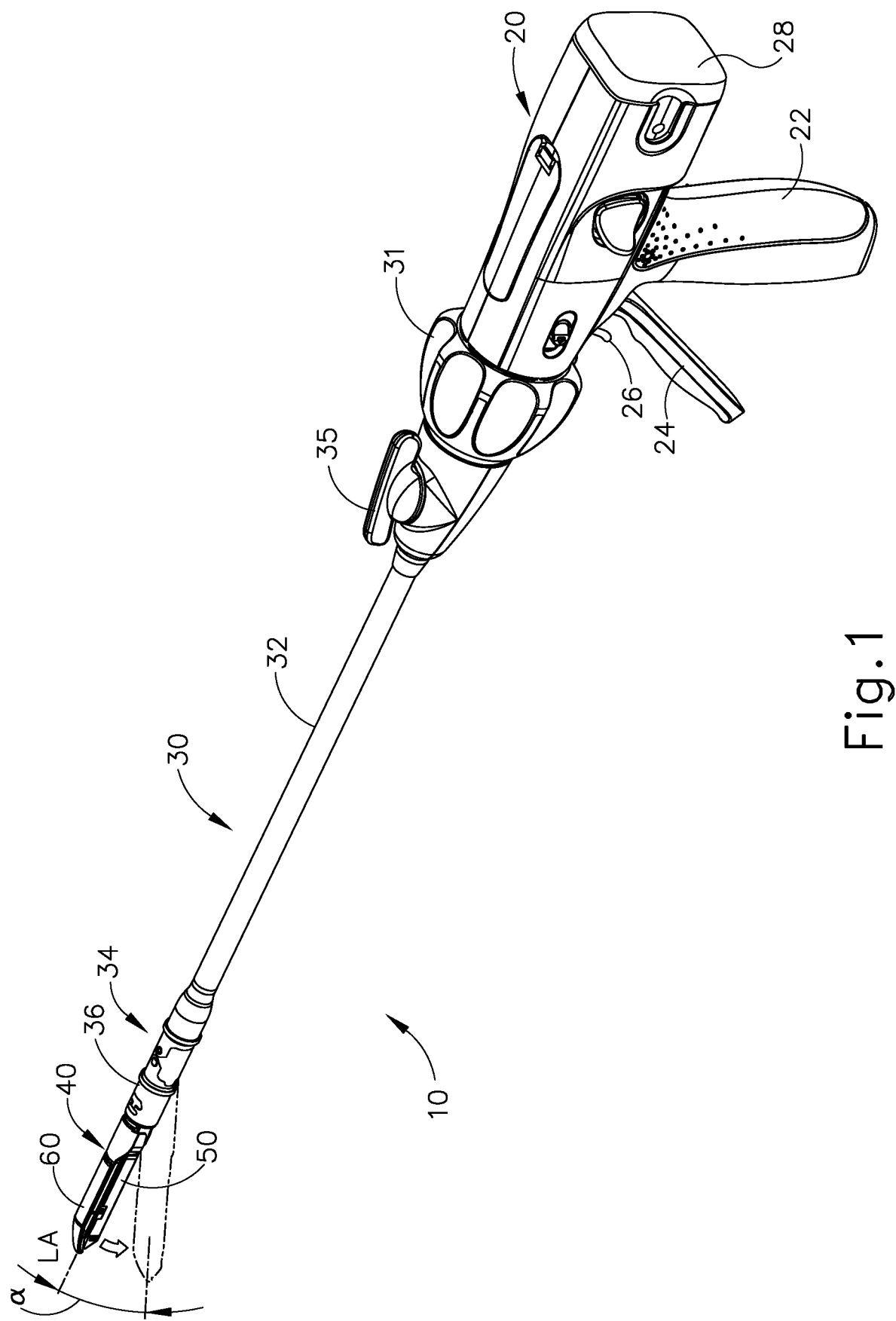
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
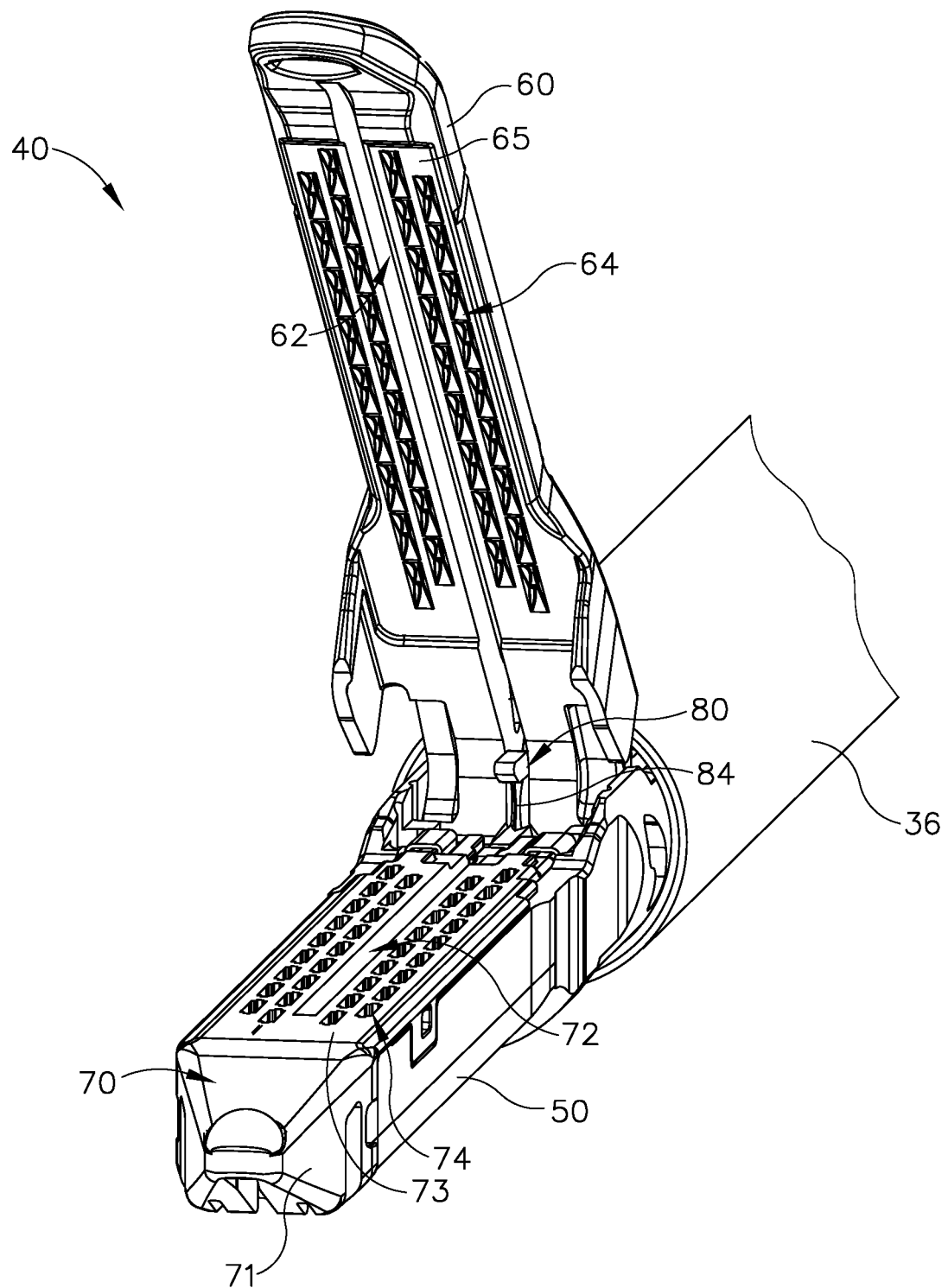
FIG. 2 depicts a perspective view of an end effector of the instrument of FIG. 1, with the end effector in an open configuration.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (a). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, the disclosure of which is incorporated by reference herein, issued as U.S. Pat. No. 9,186,142 on Nov. 17, 2015; and/or U.S. patent application Ser. No. 14/314,125, entitled "Articulation Drive Features for Surgical Stapler," filed Jun. 25, 2014, issued as U.S. Pat. No. 10,292,701 on May 21, 2019, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
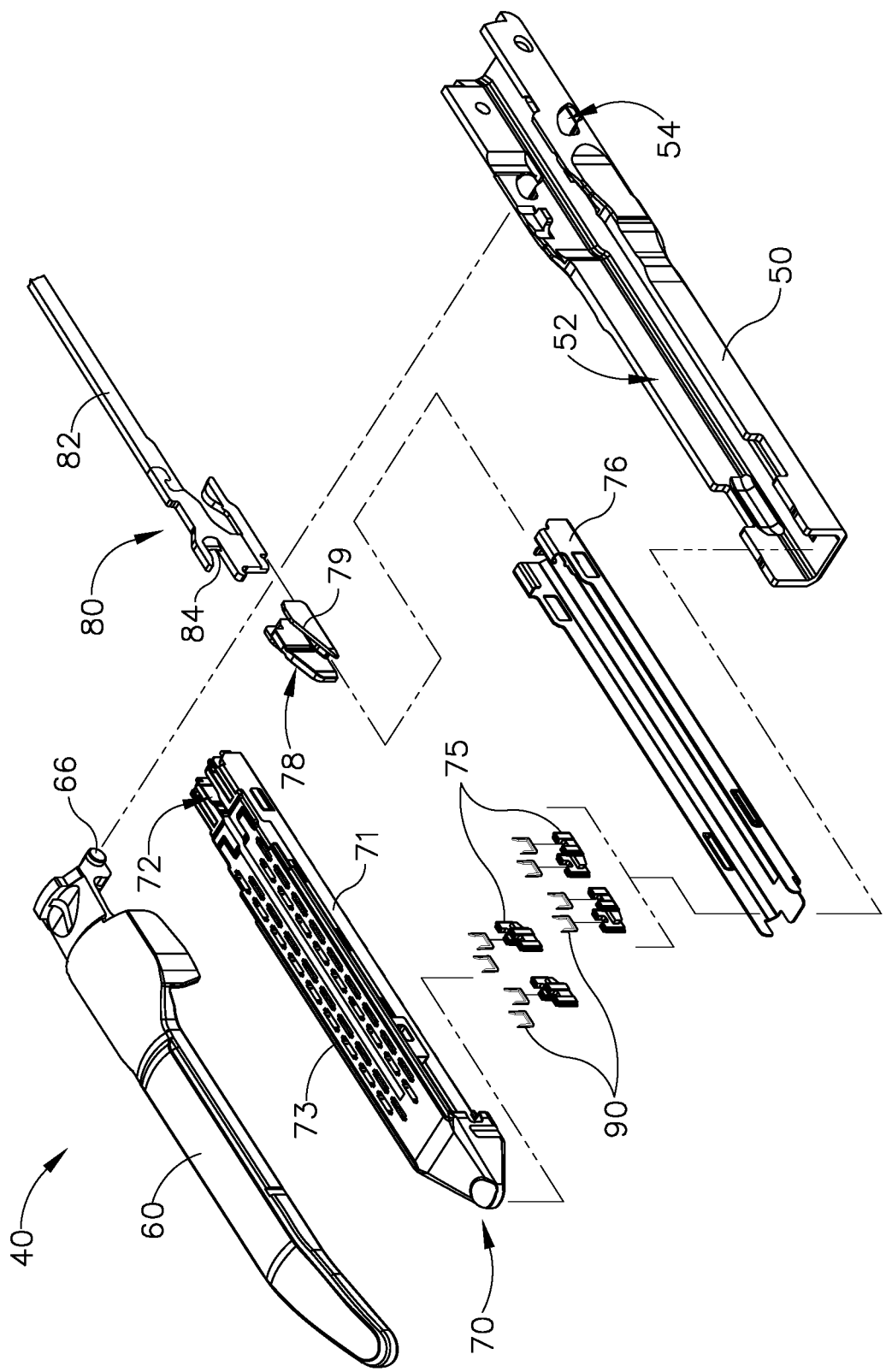
FIG. 3 depicts an exploded perspective view of the end effector of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U. U.S. Pub. No. 2014/0239042, entitled "Integrated Tissue Positioning and Jaw Alignment Features for Surgical Stapler," published Aug. 28, 2014, issued the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

In the present example, a knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, issued as U.S. Pat. No. 10,335,147 on Jul. 2, 2019, the disclosure of which is incorporated by reference herein.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein.; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. patent application Ser. No. 14/226,142, entitled "Surgical Instrument Comprising a Sensor System," filed Mar. 26, 2014, issued as U.S. Pat. No.

9,913,642 on Mar. 13, 2018, the disclosure of which is incorporated by reference herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Buttress Assembly for Surgical Stapler

In some instances, it may be desirable to equip end effector (40) with a buttress material to reinforce the mechanical fastening of tissue provided by staples (90). Such a buttress may prevent the applied staples (90) from pulling through the tissue and may otherwise reduce a risk of tissue tearing at or near the site of applied staples (90). In addition to or as an alternative to providing structural support and integrity to a line of staples (90), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress Assembly for Surgical Stapler

Figure 4:
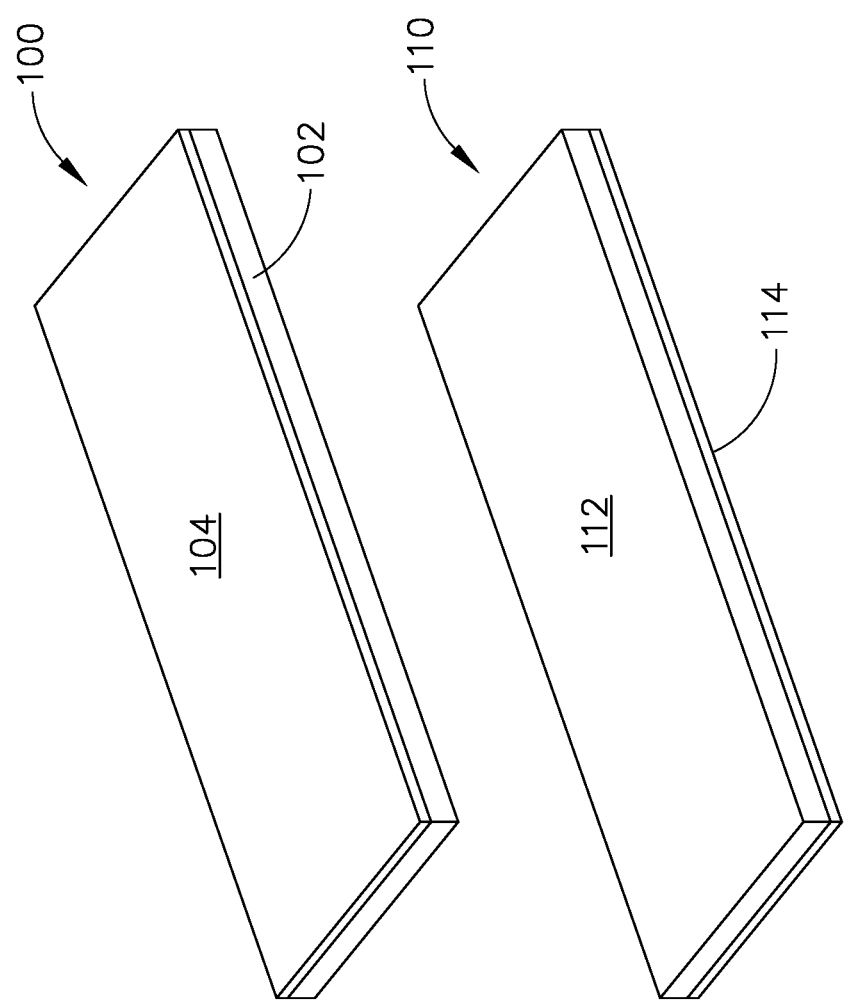
FIG. 4 depicts a perspective view of an exemplary upper buttress and an exemplary lower buttress, each of which may be applied to the end effector of FIG. 2.

FIG. 4 shows an exemplary pair of buttress assemblies (100, 110) with a basic composition. Buttress assembly (100) of this example comprises a buttress body (102) and an upper adhesive layer (104). Similarly, buttress assembly (110) comprises a buttress body (112) and a lower adhesive layer (114). In the present example, each buttress body (102, 112) comprises a strong yet flexible material configured to structurally support a line of staples (90). By way of example only, each buttress body (102, 112) may comprise a woven mesh of polyglactin 910 material by Ethicon, Inc. of Somerville, N.J. Alternatively, any other suitable materials or combinations of materials may be used in addition to or as an alternative to polyglactin 910 material to form each buttress body (102, 112). Each buttress body (102, 112) may take any other suitable form and may be constructed of any other suitable material(s). By way of further example only, each buttress body (102, 112) may comprise one or more of the following: NEOVEIL absorbable PGA felt by Gunze Limited, of Kyoto, Japan; SEAMGUARD polyglycolic acid: trimethylene carbonate (PGA: TMC) reinforcement material by W. L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGICEL NU-KNIT hemostat material by Ethicon, Inc. of Somerville, N.J. Still other suitable materials that may be used to form each buttress body (102, 112) will be apparent to those of ordinary skill in the art in view of the teachings herein.

In addition or in the alternative, each buttress body (102, 112) may comprise a material including, for example, a hemostatic agent such as fibrin to assist in coagulating blood and reduce bleeding at the severed and/or stapled surgical site along tissue (90). As another merely illustrative example, each buttress body (102, 112) may comprise other adjuncts or hemostatic agents such as thrombin may be used such that each buttress body (102, 112) may assist to coagulate blood and reduce the amount of bleeding at the surgical site. Other adjuncts or reagents that may be incorporated into each buttress body (102, 112) may further include but are not limited to medical fluid or matrix components. Merely illustrative examples of materials that may be used to form each buttress body (102, 112), as well as materials that may be otherwise incorporated into each buttress body (102, 112), are disclosed in U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein. Alternatively, any other suitable materials may be used.

By way of further example only, each buttress body (102, 112) may be constructed in accordance with at least some of the teachings of U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Patent Pub. No. 2013/0062391, entitled "Surgical Instrument with Fluid Fillable Buttress," published Mar. 14, 2013, issued as U.S. Pat. No. 9,999,408 on Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, issued as U.S. Pat. No. 8,814,025 on Aug. 26, 2014, the disclosure of which is incorporated by reference herein; U.S. Patent Pub. No. 2013/0082086, entitled "Attachment of Surgical Staple Buttress to Cartridge," published Apr. 4, 2013, issued as U.S. Pat. No. 8,899,464 on Dec. 2, 2014, the disclosure of which is incorporated by reference herein; U.S. Patent Pub. No. 2013/0037596, entitled "Device for Applying Adjunct in Endoscopic Procedure," published Feb. 14, 2013, issued as U.S. Pat. No. 9,492,170 on Nov. 15, 2016, the disclosure of which is incorporated by reference herein; U.S. Patent Pub. No. 2013/0062393, entitled "Resistive Heated Surgical Staple Cartridge with Phase Change Sealant," published Mar. 14, 2013, issued as U.S. Pat. No. 8,998,060 on Apr. 7, 2015, the disclosure of which is incorporated by reference herein; U.S. Patent Pub. No. 2013/0075446, entitled "Surgical Staple Assembly with Hemostatic Feature," published Mar. 28, 2013, issued as U.S. Pat. No. 9,393,018 on Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, issued as U.S. Pat. No. 9,101,359 on Aug. 11, 2015, the disclosure of which is incorporated by reference herein; U.S. Patent Pub. No. 2013/0075445, entitled "Anvil Cartridge for Surgical Fastening Device," published Mar. 28, 2013, issued as U.S. Pat. No. 9,198,644 on Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; U.S. Patent Pub. No. 2013/0256367, entitled "Tissue Thickness Compensator Comprising a Plurality of Medicaments," published Oct. 3, 2013, issued as U.S. Pat. No. 9,211,120 on Dec. 15, 2015, the disclosure of which is incorporated by reference herein; U.S. patent application Ser. No. 14/300,954, entitled "Adjunct Materials and Methods of Using Same in Surgical Methods for Tissue Sealing," filed Jun. 10, 2014, issued as U.S. Pat. No. 10,172,611 on Jan. 8, 2019, the disclosure of which is incorporated by reference herein; U.S. patent application Ser. No. 14/827,856, entitled "Implantable Layers for a Surgical Instrument," filed Aug. 17, 2015, issued as U.S. Pat. No. 10,835,249 on Nov. 17, 2020, the disclosure of which is incorporated by reference herein; U.S. patent application Ser. No. 14/840,613, entitled "Drug Eluting Adjuncts and Methods of Using Drug Eluting Adjuncts," filed Aug. 31, 2015, issued as U.S. Pat. No. 10,569,071 on Feb. 25, 2020, the disclosure of which is incorporated by reference herein; U.S. patent application Ser. No. 14/871,071, entitled "Compressible Adjunct with Crossing Spacer Fibers," filed Sep. 30, 2015, issued as U.S. Pat. No. 10,433,846 on Oct. 8, 2019, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein.

In the present example, adhesive layer (104) is provided on buttress body (102) in order to adhere buttress body (102) to underside (65) of anvil (60). Similarly, adhesive layer (114) is provided on buttress body (112) in order to adhere buttress body (112) to deck (73) of staple cartridge (70). Adherence of the buttress body (102) to underside (65) of anvil (60) or to deck (73) of staple cartridge (70) can occur through a variety of mechanisms including but not limited to a pressure sensitive adhesive. In some versions, each adhesive layer (104, 114) comprise a pressure sensitive adhesive material. Examples of various suitable materials that may be used to form adhesive layers (104, 114) are disclosed in U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein. Alternatively, any other suitable materials may be used. It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (104, 114) will be apparent to those of ordinary skill in the art in view of the teachings herein.

B. Exemplary Materials and Techniques for Providing Adhesion of Buttress to Surgical Stapler As noted above, a buttress assembly (100, 110) may include a layer (104, 114) of adhesive material (or other form of adhesive material) that adheres buttress body (102, 112) to either underside (65) of anvil (60) or deck (73) of staple cartridge (70). Such an adhesive material may provide proper positioning of buttress body (102, 112) before and during actuation of end effector (40); then allow buttress body (102, 112) to separate from end effector (40) after end effector (40) has been actuated, without causing damage to buttress body (102, 112) that is substantial enough to compromise the proper subsequent functioning of buttress body (102, 112).

Figure 5A:
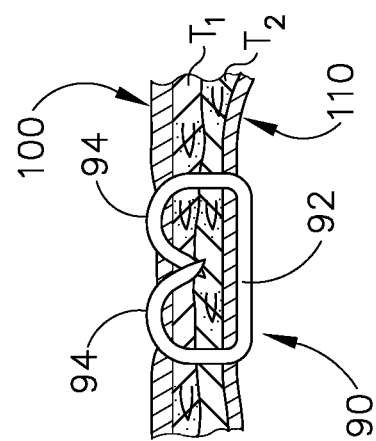
FIG. 5A depicts a cross-sectional end view of a portion of the end effector of FIG. 2 with a buttress assembly formed by the buttresses of FIG. 4 applied to the end effector, with tissue positioned between the buttresses in the end effector, and with the anvil in an open position.
Figure 5B:
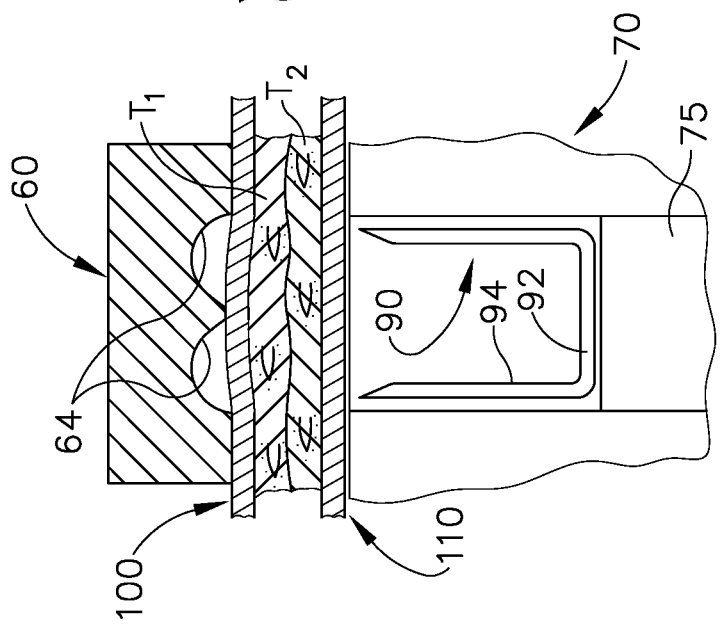
FIG. 5B depicts a cross-sectional end view of the combined end effector and buttress assembly of FIG. 5A, with tissue positioned between the buttresses in the end effector, and with the anvil in a closed position.
Figure 5C:
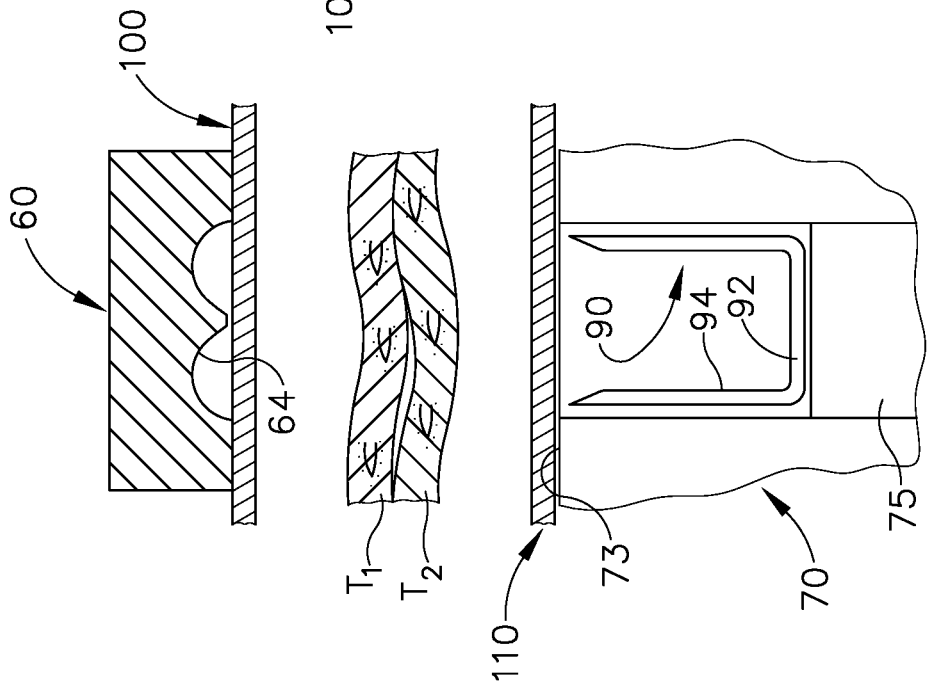
FIG. 5C depicts a cross-sectional view of a staple and the buttress assembly of FIG. 5A having been secured to the tissue by the end effector of FIG. 2.

FIGS. 5A-5C show a sequence where an end effector (40) that has been loaded with buttress assemblies (100, 110) is actuated to drive staples (90) through two apposed layers of tissue ($T_1$, $T_2$), with buttress assemblies (100, 110) being secured to the same layers of tissue ($T_1$, $T_2$) by staples (90). In particular, FIG. 5A shows layers of tissue ($T_1$, $T_2$) positioned between anvil (60) and staple cartridge (70), with anvil (60) in the open position. Buttress assembly (100) is adhered to the underside (65) of anvil (60) via adhesive layer (104); while buttress assembly (110) is adhered to deck (73) of staple cartridge (70) via adhesive layer (114). Layers of tissue ($T_1$, $T_2$) are thus interposed between buttress assemblies (100, 110). Next, trigger (24) is pivoted toward pistol grip (22) to drive closure tube (32) and closure ring (36) distally. This drives anvil (60) to the closed position as shown in FIG. 5B. At this stage, layers of tissue ($T_1$, $T_2$) are compressed between anvil (60) and staple cartridge (70), with buttress assemblies (100, 110) engaging opposite surfaces of tissue layers ($T_1$, $T_2$). End effector (40) is then actuated as described above, driving staple (90) through buttress assemblies (100, 110) and tissue (90). As shown in FIG. 5C, crown (92) of driven staple (90) captures and retains buttress assembly (110) against layer of tissue ($T_2$). Deformed legs (94) of staple (90) capture and retain buttress assembly (100) against layer of tissue ($T_1$).

Figure 6:
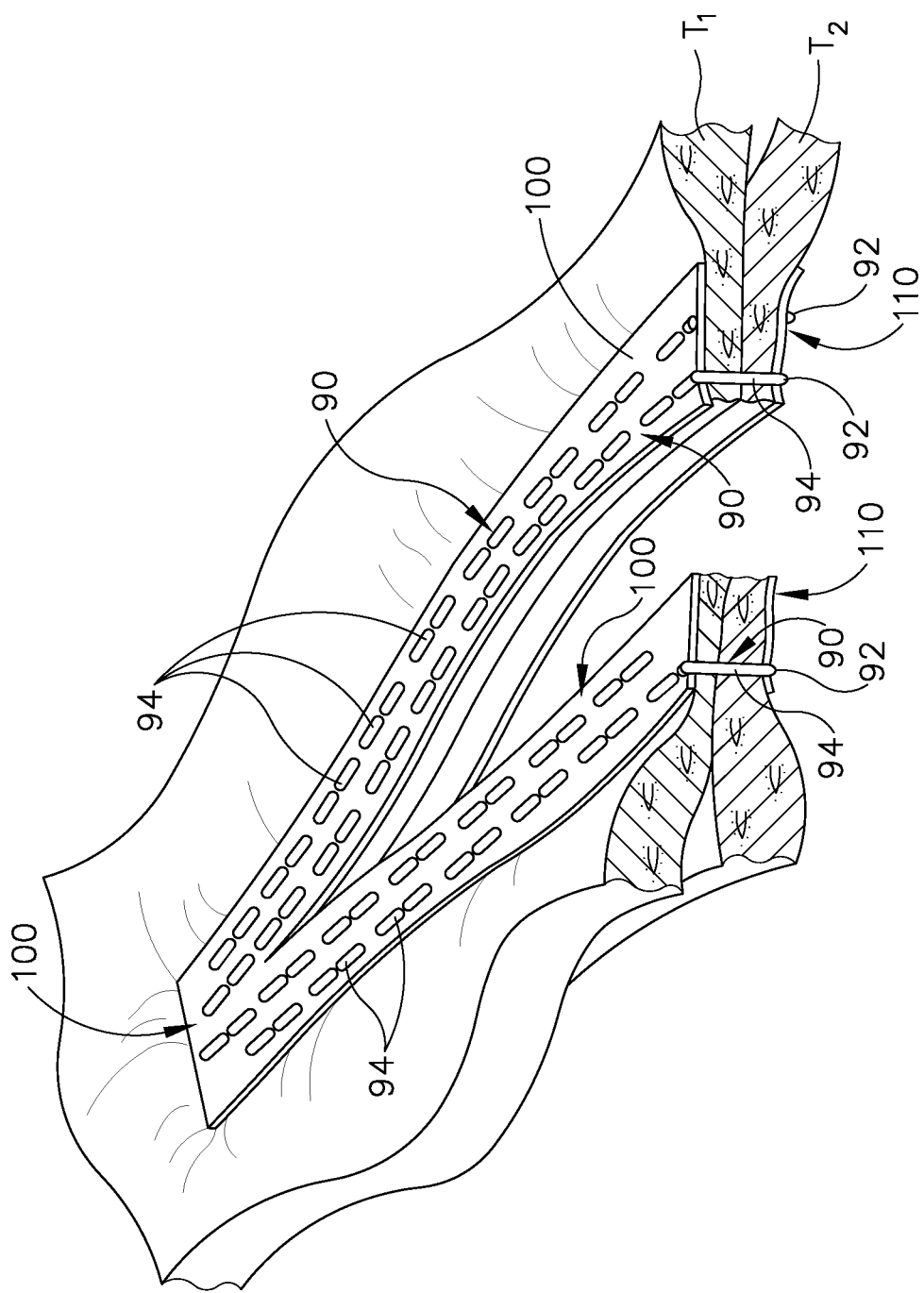
FIG. 6 depicts a perspective view of staples and the buttress assembly of FIG. 5A having been secured to the tissue by the end effector of FIG. 2.

It should be understood that a series of staples (90) will similarly capture and retain buttress assemblies (100, 110) against layers of tissue ($T_1$, $T_2$), thereby securing buttress assemblies (100, 110) to tissue ($T_1$, $T_2$) as shown in FIG. 6. As end effector (40) is pulled away from tissue (90) after deploying staples (90) and buttress assemblies (100, 110), buttress assemblies (100, 110) disengage end effector), such that buttress assemblies (100, 110) remain secured to tissue ($T_1$, $T_2$) with staples (90). Buttress tissue ($T_1$, $T_2$) thus provide structural reinforcement to the lines of staples (90). As can also be seen in FIG. 6, knife member (80) also cuts through a centerline of buttress tissue assemblies (100, 110), separating each buttress assemblies (100, 110) into a corresponding pair of sections, such that each section remains secured to a respective severed region of tissue ($T_1$, $T_2$).

In the foregoing example, buttress assembly (100) is sized to span across the full width of underside (65), such that buttress assembly (100) spans across channel (62). Thus, knife member (80) cuts through buttress assembly (100) during actuation of end effector (40) as described above. In some other examples, such as those described below, buttress assembly (100) is provided in two separate, laterally spaced apart portions, with one portion being disposed on underside (65) on one side of channel (62) and another portion being disposed on underside (65) on the other side of channel (62). In such versions, buttress assembly (100) does not span across channel (62), such that knife member (80) does not cut through buttress assembly (100) during actuation of end effector (40).

Likewise, buttress assembly (110) may be sized to span across the full width of deck (73), such that buttress assembly (110) spans across channel (72), and such that knife member (80) cuts through buttress assembly (110) during actuation of end effector (40) as described above. Alternatively, buttress assembly (110) may be provided in two separate, laterally spaced apart portions, with one portion being disposed on deck (73) on one side of channel (72) and another portion being disposed on deck (73) on the other side of channel (72), such that buttress assembly (110) does not span across channel (72), and such that knife member (80) does not cut through buttress assembly (110) during actuation of end effector (40).

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein.

III. Exemplary Buttress Applier Cartridge

As noted above, buttress assembly (100) may be applied to the underside (65) of anvil (60), and buttress (110) may be applied to deck (73) of staple cartridge (70), before tissue ($T_1$, $T_2$) is positioned in end effector (40), and before end effector (40) is actuated. Because end effector (40) may be actuated many times during use of instrument (10) in a single surgical procedure, it may be desirable to enable an operator to repeatedly and easily load buttress assemblies (100) on underside (65) of anvil (60) during that single surgical procedure. In other words, because end effector (40) may be actuated many times during use of instrument (10) in a single surgical procedure, it may be insufficient to simply provide anvil (60) pre-loaded with a buttress assembly (100) without facilitating the re-loading of anvil (60) with additional buttress assemblies (100) after end effector (40) has been actuated.

Similarly, those of ordinary skill in the art will recognize that staple cartridge (70) will need to be replaced each time end effector (40) is actuated. When end effector (40) is actuated several times during use of instrument (10) in a single surgical procedure, several staple cartridges (70) may thus be used during that surgical procedure. It may seem that each of these staple cartridges (70) may be provided with buttress assembly (110) pre-loaded on deck (73). However, there are some reasons why it may be undesirable to provide a staple cartridge (70) with buttress assembly (110) pre-loaded on deck (73). In other words, it may be desirable to provide loading of buttress assembly (110) on deck (73) immediately prior to usage of staple cartridge in the surgical procedure, rather than loading buttress assembly (110) on deck (73) a substantial time prior to the surgical procedure. For instance, buttress assembly (110) may not be compatible with the same sterilization techniques as staple cartridge (70), such that it may present processing difficulties to package staple cartridge (70) with buttress assembly (110) pre-loaded on deck (73). In addition, the material forming buttress assembly (110) may have certain environmental sensitivities that staple cartridge (70) does not have, such that it may be beneficial to enable buttress assembly (110) and staple cartridge (70) to be stored separately before use. Moreover, buttress assembly (110) may not be warranted or otherwise desired in some surgical procedures, such that it may be desirable to enable a physician to easily choose whether staple cartridge (70) should be loaded with buttress assembly (110) before that staple cartridge (70) is used in the surgical procedure.

In view of the foregoing, it may be desirable to enable an operator to repeatedly and easily load buttress assemblies (100, 110) on end effector (40) on an ad hoc basis during a given surgical procedure. It may also be desirable to provide a device that provides support and protection to buttress assemblies (100, 110) before buttress assemblies (100, 110) are loaded on end effector (40), in addition to that same device also enabling buttress assemblies (100, 110) to be easily loaded on end effector. The examples described below relate to various cartridge assemblies that provide such support, protection, and loading of buttress assemblies (100, 110). It should be understood that the following examples are merely illustrative. Numerous variations will be apparent to those of ordinary skill in the art in view of the teachings herein.

Figure 7:
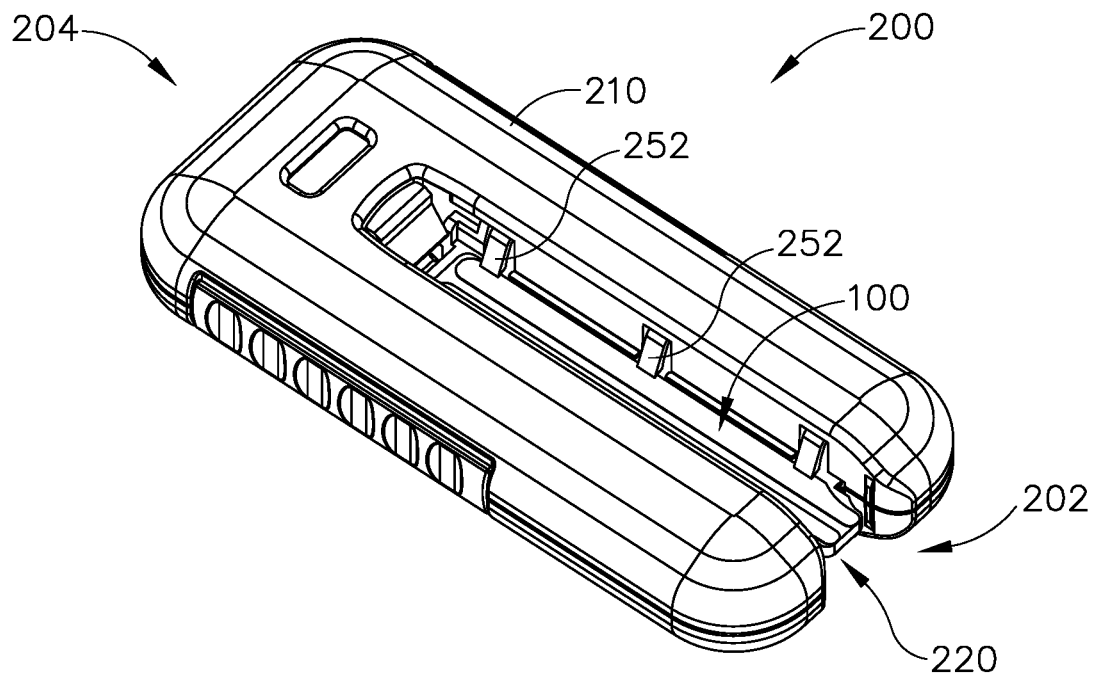
FIG. 7 depicts a perspective view of an exemplary buttress applier cartridge that may be used to carry and apply the buttress assembly of FIG. 5A.
Figure 8:
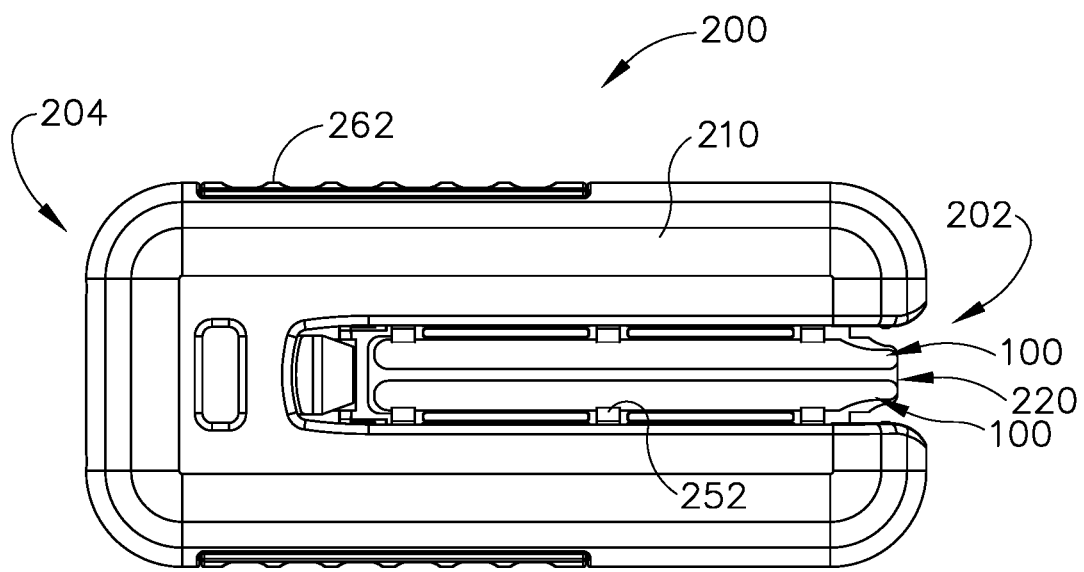
FIG. 8 depicts a top plan view of the buttress applier cartridge of FIG. 7.

FIGS. 7-9B show an exemplary buttress applier cartridge (200) that may be used to support and protect buttress assemblies (100, 110). Cartridge (200) may also be used to easily load buttress assemblies (100, 110) on end effector (40). As best seen in FIGS. 7-8, cartridge (200) of this example comprises an open end (202) and a closed end (204). Open end (202) is configured to receive end effector (40) as will be described in greater detail below. Cartridge (200) further includes a first housing (210) that generally defines a "U" shape to present open end (202). Cartridge (200) further includes a platform (220) and a set of retainers (252). Platform (220) of the present example is configured to support a pair of buttress assemblies (100) via retainer arms (252) on one side of platform (220) and another pair of buttress assemblies (110) on the other side of platform (220) via retainer arms (252). Platform (220) is exposed in recesses that are formed between the prongs of the "U" configuration of housing (210). The location of platform (220) and buttress assemblies (100, 110) in such recesses may prevent inadvertent contact between buttress assemblies (100, 110) and other devices in the operating room. In other words, housings (210, 218) may provide some degree of physical shielding of buttress assemblies (100, 110).

In the present example, each buttress assembly (100, 110) is provided in a respective pair of portions that are separated to avoid spanning across channels (62, 72) of anvil (60) and staple cartridge (70), respectively, though it should be understood that platform (220) may just as easily support wide versions of buttress assemblies (100, 110) that unitarily span across channels (62, 72) of anvil (60) and staple cartridge (70), respectively. The outer edges of platform (220) are captured within housing (210) and include retention features to prevent platform (220) from sliding relative to housing (210). In some versions, platform (220) is formed of a material that provides a high coefficient of friction, thereby reducing any tendency that buttress assemblies (100, 110) might otherwise have to slide along corresponding surfaces of platform (220). For instance, platform (220) may comprise an elastomeric material and/or a foam material. In some instances, platform (220) is formed of a compressible foam material that is configured to maintain a compressed configuration after being compressed by end effector (40). By way of example only, platform (220) may comprise Santoprene, closed-cell polyurethane foam, any other compressible material, and/or a material that may be made compressible via geometry (e.g., a rubber material with deformable standing features). Various suitable materials and structural configurations that may be used to form platform (220) will be apparent to those of ordinary skill in the art in view of the teachings herein.

Retainer arms (252) of the present example are configured to selectively secure buttress assemblies (100, 110) to platform (220). In particular, buttress assemblies (100, 110) are interposed between the free ends of arms (252) and platform (220). In the present example, retainer arms (252) are movable laterally outwardly such that retainer arms (252) disengage buttress assemblies (100, 110), thereby enabling buttress assemblies (100, 110) to be removed from platform (220). Retainer arms (252) are resilient and are thus configured to resiliently bear against buttress assemblies (100, 110), thereby pinching buttress assemblies (100, 110) against platform (220). Other suitable ways in which retainer arms (252) may engage buttress assemblies (100, 110) will be apparent to those of ordinary skill in the art in view of the teachings herein.

Figure 9A:
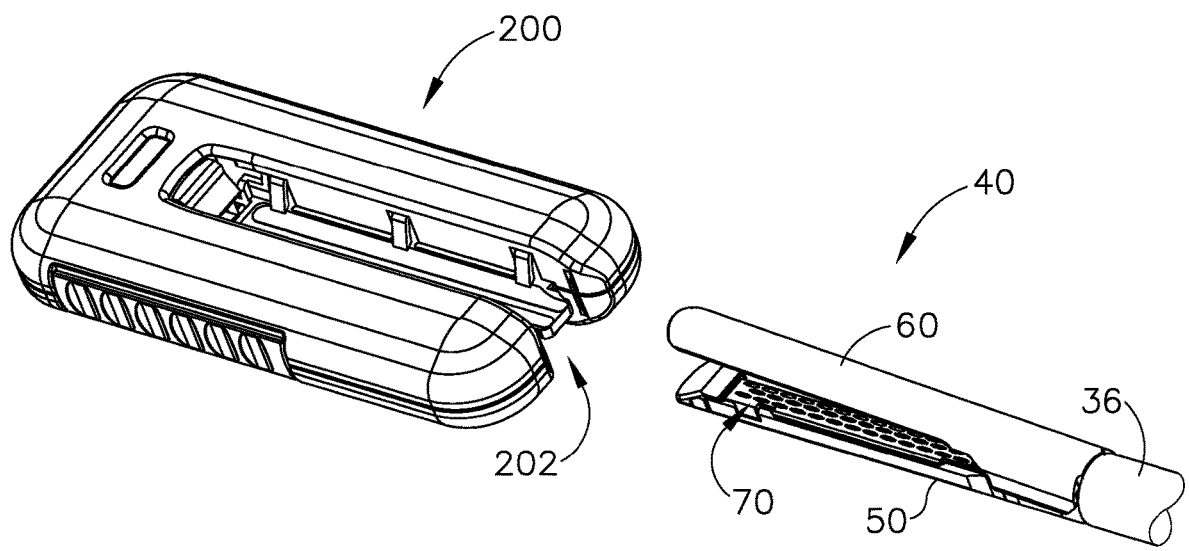
FIG. 9A depicts a perspective view of the end effector of FIG. 2 and the buttress applier cartridge of FIG. 7, with the end effector approaching the buttress applier cartridge.
Figure 9B:
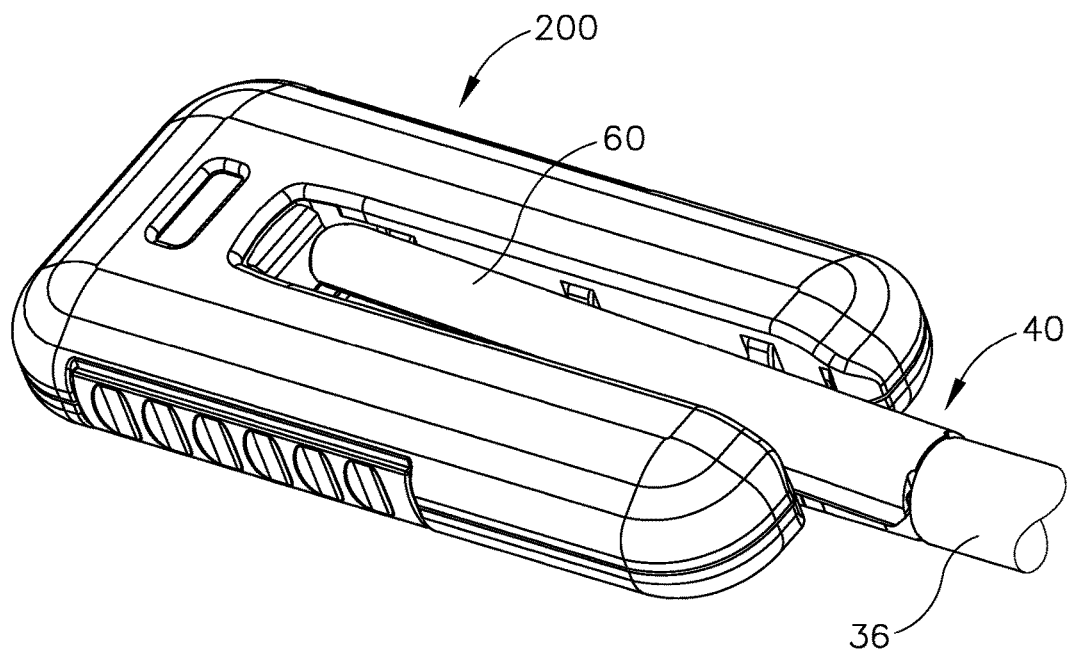
FIG. 9B depicts a perspective view of the end effector of FIG. 2 and the buttress applier cartridge of FIG. 7, with the buttress applier cartridge positioned in the end effector.

To use cartridge (200) to load end effector (40), the operator would first position cartridge (200) and end effector (40) such that end effector is aligned with open end (202) of cartridge (200) as shown in FIG. 9A. The operator would then advance end effector (40) distally (and/or retract cartridge (200) proximally) to position platform (220) and buttress assemblies (100, 110) between anvil (60) and staple cartridge (70) as shown in FIG. 9B. In order to load buttress assemblies (100, 110) on end effector (40), the operator may simply close end effector (40) by pivoting anvil (60) toward staple cartridge (70), as described above. Such closure of end effector (40) will result in disengagement of retainer arms (252) from buttress assemblies (100, 110). With end effector (40) clamping on both buttress assemblies (100, 110), adhesive layers (104, 114) are adhered to underside (65) of anvil (60) and deck (73) of staple cartridge (70). End effector (40) may then be re-opened (i.e., pivoting anvil (60) away from staple cartridge (70)) and pulled away from cartridge (200). With retainer arms (252) disengaged from buttress assemblies (100, 110), end effector (40) may freely pull buttress assemblies (100, 110) away from platform (220) as end effector (40) is pulled away from cartridge (200). With buttress assemblies (100, 110) loaded on end effector (40), end effector (40) may then be used as described above with reference to FIGS. 5A-6.

In addition to or in lieu of the foregoing, cartridge (200) may be constructed and operable in accordance with at least some of the teachings of U.S. Patent App. No. 62/209,041, entitled "Method and Apparatus for Applying a Buttress to End Effector of a Surgical Stapler," filed Aug. 25, 2015, the disclosure of which is incorporated by reference herein.

IV. Exemplary Features to Control and Indicate Humidity Conditions in Buttress Applier Cartridge Some versions of buttress assemblies (100, 110) may include features that are sensitive to humidity conditions. For instance, the material forming body (102, 112) may be sensitive to humidity conditions in a way such that the effectiveness of body (102, 112) is adversely affected when body (102, 112) is exposed to humidity for a prolonged period. Similarly, the material forming adhesive layer (104, 114) may be sensitive to humidity conditions in a way such that the effectiveness of adhesive layer (104, 114) is adversely affected when adhesive layer (104, 114) is exposed to humidity for a prolonged period. It may therefore be desirable to incorporate one or more features into a buttress applier cartridge that is/are configured to prevent buttress assemblies (100, 110) from being exposed to humidity for prolonged periods. In addition, it may be desirable to incorporate one or more features into a buttress applier cartridge that is/are configured to indicate if buttress assemblies (100, 110) have been exposed to humidity for prolonged periods. If such an indicator shows that buttress assemblies (100, 110) have been exposed to humidity for prolonged periods, the operator may avoid using those particular buttress assemblies (100, 110).

Figure 10:
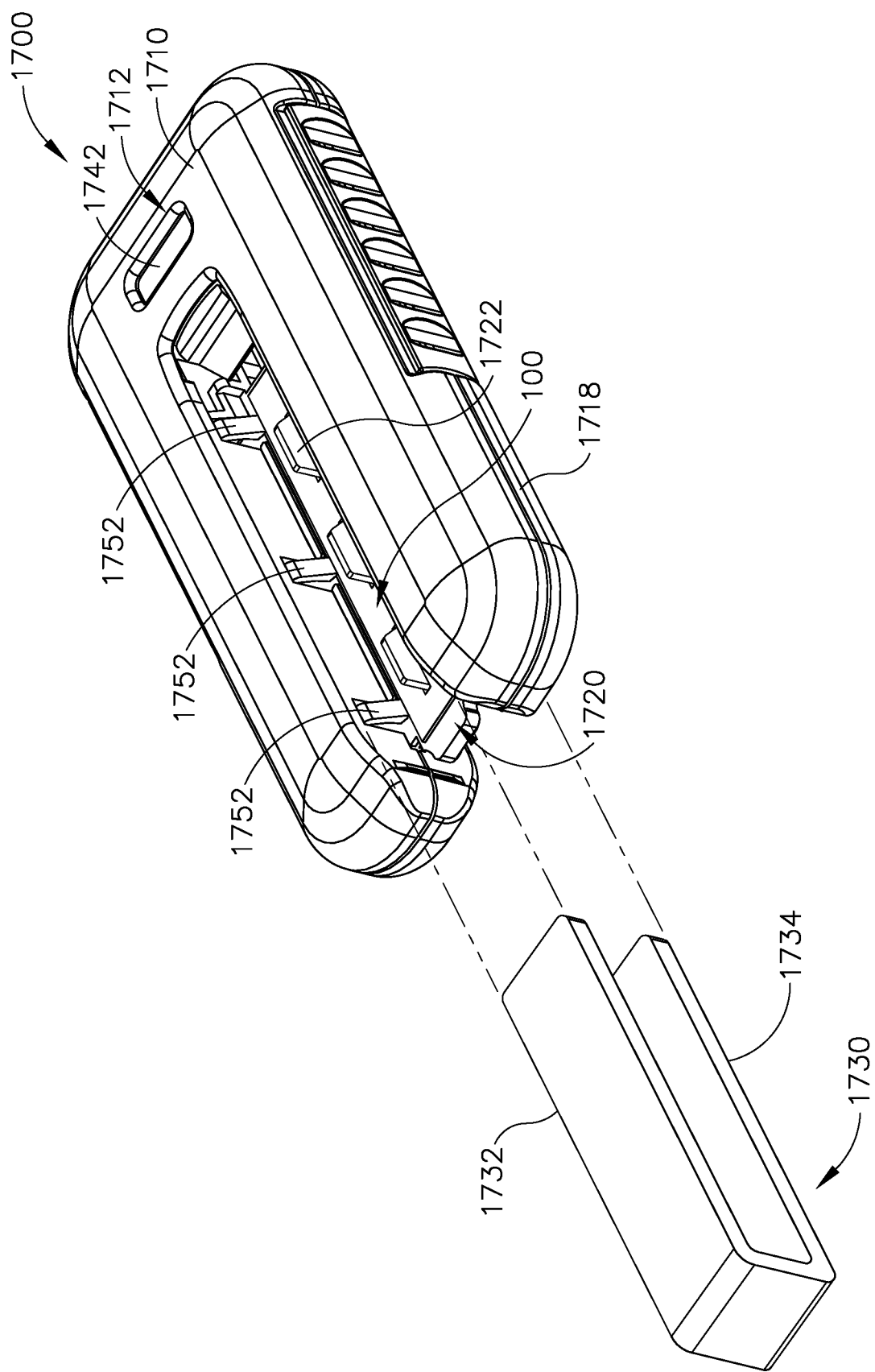
FIG. 10 depicts a perspective view of another exemplary alternative buttress applier cartridge.

FIG. 10 shows an exemplary buttress applier cartridge (1700) that includes housings (1710, 1718), a platform (1720) supporting a buttress assembly (100), and a plurality of retention features (1752). Retention features (1752) are configured to releasably secure buttress assembly (100) to platform (1720); and may be configured like any of the various retention features described herein. Platform (1720) includes a plurality of fins (1722). Fins (1722) are configured to fit within the sidewalls defining channel (62) to ensure that anvil (60) is properly aligned with buttress assembly (100) as anvil (60) is closed down toward buttress assembly (100) and platform (1720). It should also be understood that the underside of platform (1720) (i.e., the side carrying buttress assembly (110), associated with staple cartridge (70)), may also include fins (1722). Fins (1722) on the underside of platform (1720) may be sized and arranged to fit in channel (72) of staple cartridge (70). Moreover, as will be described in greater detail below, fins (1722) on the underside of platform (1720) may be configured to prevent cartridge (1700) from being used with a staple cartridge (70) that has already been fired.

Cartridge (1700) of the present example further includes a plurality of indicator beads (1742) that are viewable through a window (1712) formed in housing (1710). Indicator beads (1742) are formed of a color-changing desiccant material. In particular, beads (1742) are configured to reflect a first color when beads (1742) are in a substantially dry state; and a second color when beads (1742) are in a wet state. Beads (1742) may transition to a wet state in response to exposure to humidity that is above a threshold that is suitable for buttress assemblies (100, 110). In some versions, beads (1742) will maintain the second color even if the humidity level later drops back below the threshold level. Beads (1742) will thus provide visual indication to the user to indicate that buttress assemblies (100, 110) have been subject to an unacceptable level of humidity. Of course, beads (1742) may also transition from the first color to the second color if beads (1742) are otherwise exposed to fluid, such as spilled medical fluids, bodily fluids from a patient, etc. Various materials that may be used to form beads (1742) will be apparent to those of ordinary skill in the art in view of the teachings herein.

Cartridge (1700) of the present example further includes a cover (1730) that may be removably secured to housings (1710, 1718). Cover (1730) includes an upper panel (1732) and a lower panel (1734) that are coupled together to define a "U" shape. Cover (1730) is sized and configured to cover the recesses in which platform (1720) and buttress assemblies (100, 110) are disposed when cover (1730) is secured to housings (1710, 1718). Cover (1730) may thus protect buttress assemblies (100, 110) up until an operator is ready to use cartridge (1700). To remove cover (1730), the operator may simply pull cover (1730) away from cartridge (1700). By way of example only, panels (1732, 1734) may be resiliently biased toward each other such that panels (1732, 1734) are oriented to be non-parallel with each other. Thus, panels (1732, 1734) may be deflected away from each other to reach a parallel state when cover (1730) is engaged with housings (1710, 1718), such that panels (1732, 1734) resiliently bear against housings (1710, 1718) to provide a secure fit through friction. Various other suitable configurations that may be used to form cover (1730), and to secure cover (1730) to housings (1710, 1718), will be apparent to those of ordinary skill in the art in view of the teachings herein. It should also be understood that cover (1730) may be used with any of the buttress applier cartridges described herein, such that cover (1730) is not at all limited to cartridge (1700).

In some versions, cover (1730) comprises a desiccant material that is configured to absorb moisture (e.g., from humidity) and thereby prevent that moisture from reaching buttress assemblies (100, 110). In addition or in the alternative, desiccant material may be incorporated into the material forming platform (1720), the material forming housing (1710), packets or compartments located within a cavity defined by housing (1710, 1718), and/or in various other suitable locations/configurations. By way of example only, silica gel may be included in packets that are located within a cavity defined by housing (1710, 1718). Other suitable desiccant materials that may be incorporated into cartridge (1700) will be apparent to those of ordinary skill in the art in view of the teachings herein. Similarly, various other ways in which one or more desiccant materials may be incorporated into cartridge (1700) will be apparent to those of ordinary skill in the art in view of the teachings herein.

V. Exemplary Features to Prevent Use of Buttress Applier Cartridge with Spent Staple Cartridge In the present example, after a staple cartridge (70) has been actuated once, that staple cartridge (70) cannot be used again in the same surgical procedure. This is because all of the staples (90) in staple cartridge (70) will have been deployed, such that a spent staple cartridge (70) will be unable to apply more staples (90). Instrument (10) may include various features that are sensitive to the spent state of a staple cartridge (70), such that instrument may prevent firing beam (82) from being actuated as second time through a spent staple cartridge (70). In view of this, it may be desirable to prevent an operator from improperly or inadvertently using a buttress applier cartridge to apply buttress assemblies (100, 110) to an end effector (40) that has a spent staple cartridge (70) loaded in lower jaw (50).

Figure 11:
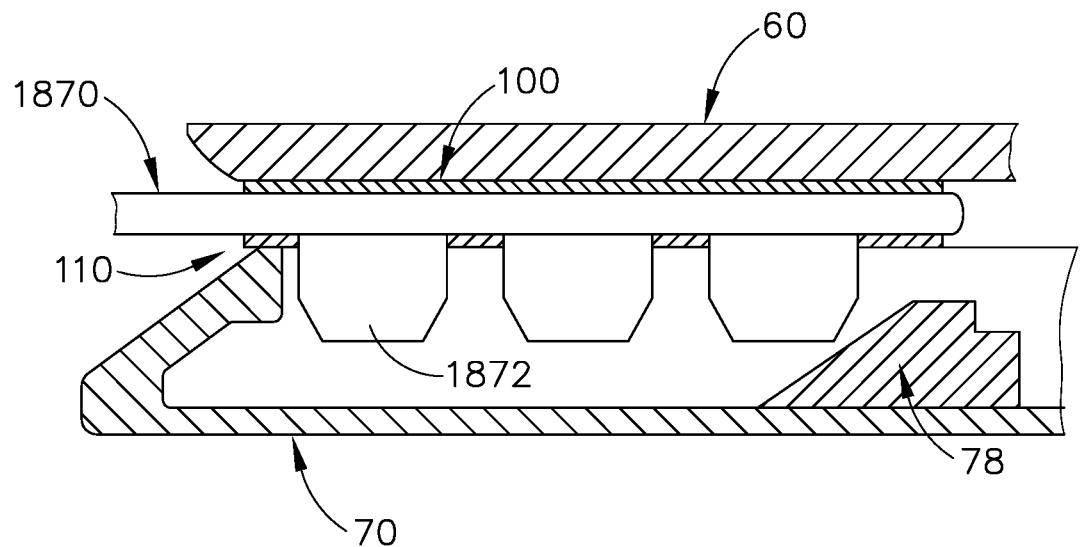
FIG. 11 depicts a cross-sectional side view of another exemplary alternative buttress applier cartridge, similar to the buttress applier cartridge of FIG. 10, with the end effector of FIG. 2 positioned about a platform of the buttress applier cartridge, with the end effector in a closed configuration, and with a staple cartridge of the end effector in a non-spent state.
Figure 12:
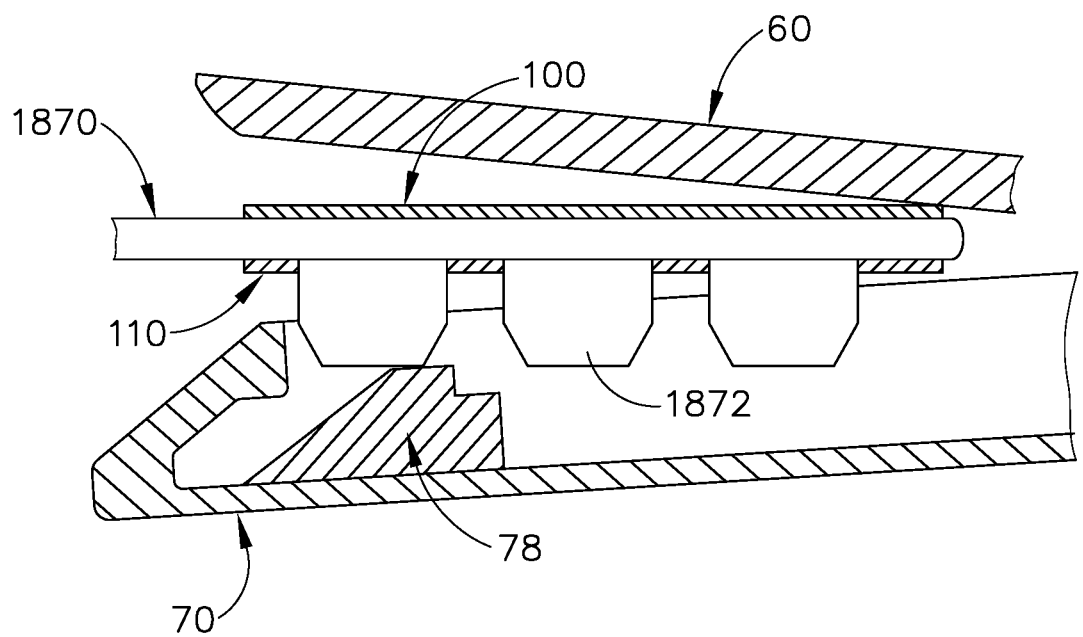
FIG. 12 depicts a cross-sectional side view of the buttress applier cartridge of FIG. 11, with the end effector of FIG. 2 positioned about a platform of the buttress applier cartridge, with the end effector in a partially closed configuration, and with a staple cartridge of the end effector in a spent state.

To that end, FIGS. 11-12 show exemplary features that may be readily incorporated into any of the buttress applier cartridges described herein to prevent the buttress applier cartridge from being used to apply buttress assemblies (100, 110) to an end effector (40) that has a spent staple cartridge (70) loaded in lower jaw (50). In particular, FIGS. 11-12 show a platform (1870) that has a plurality of integral, downwardly extending rigid fins (1872). Fins (1872) of this example are substantially identical to fins (1722) described above, such that fins (1872) are sized and configured to fit in channel (72) of staple cartridge (70). It should therefore be understood that fins (1872) may assist in ensuring proper alignment between buttress assembly (110) and staple cartridge (70).

Fins (1872) will also provide a lockout to prevent full closure of an end effector (40) that includes a spent staple cartridge (70). As shown in FIG. 11, in a non-spent staple cartridge (70), wedge sled (78) is located at a proximal position. Fins (1872) are configured and positioned such that no fin (1872) will engage the proximally positioned wedge sled (78) when end effector (40) is closed on buttress assemblies (100, 110) and platform (1870). In other words, fins (1872) will not prevent full closure of end effector (40) about buttress assemblies (100, 110) and platform (1870) when staple cartridge (70) is in a non-spent state. However, FIG. 12 shows how wedge sled (78) is positioned distally in a spent staple cartridge (70); and how one of the fins (1872) will engage the distally positioned wedge sled (78) to prevent full closure of end effector (40) about buttress assemblies (100, 110) and platform (1870) when staple cartridge (70) is in a spent state. It should therefore be understood that fins (1872) will prevent the operator from being able to apply buttress assembly (110) to deck (73) of a spent staple cartridge (70). Moreover, by physically obstructing full closure of end effector (40) about buttress assemblies (100, 110), fins (1872) will provide the operator with visual and tactile feedback indicating that the operator is improperly attempting to use an end effector (40) with a spent staple cartridge (70).

While platform (1870) only includes downwardly extending fins (1872) in this example, it should be understood that platform (1872) may also include upwardly extending fins like fins (1722) described above. To the extent that such upwardly extending fins may not prevent full closure of end effector (40) about buttress assemblies (100, 110) and platform (1870) when staple cartridge (70) is in a spent state, the upwardly extending fins may nevertheless promote proper alignment between end effector (40) and buttress assemblies (100, 110) as described above.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a housing defining a gap configured to receive a portion of an end effector of a surgical stapler; (b) a platform, wherein a portion of the platform is exposed in the gap defined by the housing; (c) a first buttress assembly positioned on the platform, wherein the buttress assembly is exposed in the gap defined by the housing; and (d) at least one retainer member configured to selectively retain the first buttress assembly against the platform, wherein the at least one retainer member is further configured to release the first buttress assembly from the platform in response to a clamping action of an end effector positioned in the gap defined by the housing.

Example 2

The apparatus of Example 1, wherein the housing defines a U shape.

Example 3

The apparatus of any one or more of Examples 1 through 2, wherein the platform is formed of a compressible material.

Example 4

The apparatus of any one or more of Examples 1 through 3, wherein the first buttress assembly comprises: (i) a body, and (ii) an adhesive layer

Example 5

The apparatus of Example 4, wherein the adhesive layer is exposed in the gap defined by the housing.

Example 6

The apparatus of any one or more of Examples 1 through 5, further comprising a second buttress assembly, wherein the first buttress assembly is positioned on a first side of the platform, wherein the second buttress assembly is positioned on a second side of the platform.

Example 7

The apparatus of any one or more of Examples 1 through 6, wherein the first buttress assembly comprises: (i) a first longitudinally extending portion, and (ii) a second longitudinally extending portion, wherein the second longitudinally extending portion is laterally spaced apart from the first longitudinally extending portion.

Example 8

The apparatus of Example 7, wherein the second longitudinally extending portion is laterally spaced apart from the first longitudinally extending portion by a distance corresponding to a width of a gap defined by a channel formed in an end effector in a surgical stapler.

Example 9

The apparatus of any one or more of Examples 1 through 70, further comprising a desiccant material disposed on or in the housing.

Example 10

The apparatus of Example 9, wherein the desiccant material is configured to change color in response to the presence of moisture.

Example 11

The apparatus of Example 10, wherein the housing defines a window, wherein the desiccant material is viewable through the window.

Example 12

The apparatus of any one or more of Examples 1 through 11, further comprising a cover removably coupled with the housing, wherein the cover is configured to selectively cover the gap defined by the housing.

Example 13

The apparatus of 12, wherein the cover comprises a desiccant material.

Example 14

The apparatus of any one or more of Examples 1 through 13, wherein the platform comprises at least one fin, wherein the at least one fin is configured to engage a distally positioned wedge sled of a spent staple cartridge in response to a clamping action of an end effector positioned in the gap defined by the housing, thereby preventing full closure of the end effector about the platform.

Example 15

An apparatus comprising: (a) a housing defining a gap configured to receive a portion of an end effector of a surgical stapler; (b) a platform, wherein a portion of the platform is exposed in the gap defined by the housing; (c) a first buttress assembly positioned on the platform, wherein the first buttress assembly is exposed in the gap defined by the housing; and (d) a lockout feature, wherein the lockout feature is configured to enable an end effector with an unspent staple cartridge to clamp onto the platform and thereby engage the first buttress assembly, wherein the lockout feature is further configured to prevent an end effector with a spent staple cartridge from clamping onto the platform to thereby engage the first buttress assembly.

Example 16

The apparatus of Example 15, wherein the lockout feature comprises at least one fin extending from the platform.

Example 17

The apparatus of Example 16, wherein the at least one fin is configured to engage a distally positioned wedge sled of a spent staple cartridge in response to a clamping action of an end effector positioned in the gap defined by the housing, thereby preventing full closure of the end effector about the platform.

Example 18

The apparatus of any one or more of Examples 16 through 17, wherein the lockout feature comprises a plurality of fins extending from the platform, wherein the plurality of fins are arranged in a longitudinally extending array.

Example 19

The apparatus of any one or more of Examples 15 through 18, wherein the at least one fin is rigid.

Example 20

The apparatus of any one or more of Examples 15 through 19, further comprising at least one retainer member configured to selectively retain the first buttress assembly against the platform, wherein the at least one retainer member is further configured to release the first buttress assembly from the platform in response to a clamping action of an end effector positioned in the gap defined by the housing.

Example 21

The apparatus of any one or more of Examples 15 through 20, further comprising a second buttress assembly, wherein the first buttress assembly is positioned on a first side of the platform, wherein the second buttress assembly is positioned on a second side of the platform.

Example 22

The apparatus of Example 21, wherein the lockout feature is adjacent to the second buttress assembly

Example 23

A kit comprising: (a) a buttress applier cartridge, wherein the buttress applier cartridge comprises: (i) a housing defining a gap configured to receive a portion of an end effector of a surgical stapler, (ii) a platform, wherein a portion of the platform is exposed in the gap defined by the housing, (iii) a first buttress assembly positioned on the platform, wherein the first buttress assembly is exposed in the gap defined by the housing, and (iv) a lockout feature, wherein the lockout feature is configured to enable an end effector with an unspent staple cartridge to clamp onto the platform and thereby engage the first buttress assembly, wherein the lockout feature is further configured to prevent an end effector with a spent staple cartridge from clamping onto the platform to thereby engage the first buttress assembly; and (b) a stapling instrument having an end effector, wherein the end effector comprises: (i) an anvil, and (ii) a staple cartridge, wherein the anvil is movable toward the staple cartridge to provide the end effector in a closed configuration, wherein the staple cartridge comprises a movable actuation member, wherein the actuation member is movable from a first position to a second position to drive staples from the staple cartridge toward the anvil; wherein the lockout feature is configured to permit the end effector to reach the closed configuration about the platform and buttress assembly when the actuation member is in the first position, wherein the lockout feature is configured to prevent the end effector from reaching the closed configuration about the platform and buttress assembly when the actuation member is in the second position.

Example 24

A method of securing a buttress to an end effector, wherein the end effector comprises an upper jaw member and a lower jaw member, the method comprising: (a) positioning a platform of a buttress applier cartridge between the upper and lower jaw members while the upper and lower jaw members are in an open configuration, wherein the platform has a buttress disposed thereon during the act of positioning the platform between the upper and lower jaw members; (b) driving one or both of the upper or lower jaw members toward the platform to thereby engage the buttress with the end effector, wherein the buttress applier cartridge further comprises at least one fin that enters a channel in a staple cartridge of the end effector during the act of driving one or both of the upper or lower jaw members toward the platform to thereby engage the buttress with the end effector, wherein the staple cartridge further comprises a slidable staple actuation member that is located in a proximal position relative to the fin during the act of driving one or both of the upper or lower jaw members toward the platform to thereby engage the buttress with the end effector; and (c) driving one or both of the upper or lower jaw members way from the platform to thereby pull the buttress off of the platform.

VII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein; U.S. patent application Ser. No. 14/827,856, entitled "Implantable Layers for a Surgical Instrument," filed Aug. 17, 2015, issued as U.S. Pat. No. 10,835,249 on Nov. 17, 2020, the disclosure of which is incorporated by reference herein; U.S. patent application Ser. No. 14/871,071, entitled "Compressible Adjunct with Crossing Spacer Fibers," filed Sep. 30, 2015, issued as U.S. Pat. No. 10,433,846 on Oct. 8, 2019, the disclosure of which is incorporated by reference herein; and U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein. Furthermore, in addition to the methods described herein, any of the various buttress assemblies described herein may be applied to end effector (40) in accordance with at least some of the teachings of U.S. Provisional Patent App. No. 62/209,041, entitled "Method and Apparatus for Applying a Buttress to End Effector of a Surgical Stapler," filed Aug. 24, 2015, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein. Various suitable ways in which the teachings herein may be combined with various teachings of the above-cited references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012; issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A standalone buttress applicator, configured to apply a buttress material to an end effector of a surgical stapler comprising:
(a) a housing defining a gap configured to receive a portion of an end effector of a surgical stapler;
(b) a platform, wherein a portion of the platform is exposed in the gap defined by the housing;

(c) a first buttress assembly positioned on the platform, wherein the first buttress assembly is exposed in the gap defined by the housing; and (d) a lockout feature protruding outwardly relative to the platform, wherein the lockout feature is configured to enable an end effector with an unspent staple cartridge to clamp onto the platform and thereby engage the first buttress assembly, wherein the lockout feature is further configured to prevent an end effector with a spent staple cartridge from clamping onto the platform to thereby engage the first buttress assembly.

2. The buttress applicator of claim 1, wherein the lockout feature comprises at least one fin extending from the platform.

3. The buttress applicator of claim 2, wherein the at least one fin is configured to engage a distally positioned wedge sled of a spent staple cartridge in response to a clamping action of an end effector positioned in the gap defined by the housing, thereby preventing full closure of the end effector about the platform.

4. The buttress applicator of claim 2, wherein the lockout feature comprises a plurality of fins extending from the platform, wherein the plurality of fins are arranged in a longitudinally extending array.

5. The buttress applicator of claim 2, wherein the at least one fin is rigid.

6. The buttress applicator of claim 1, further comprising at least one retainer member configured to selectively retain the first buttress assembly against the platform, wherein the at least one retainer member is further configured to release the first buttress assembly from the platform in response to a clamping action of an end effector positioned in the gap defined by the housing.

7. The buttress applicator of claim 1, wherein the housing defines a U shape.

8. The buttress applicator of claim 1, wherein the platform is formed of a compressible material.

9. The buttress applicator of claim 1, wherein the first buttress assembly comprises:
(i) a body, and
(ii) an adhesive layer.

10. The buttress applicator of claim 9, wherein the adhesive layer is exposed in the gap defined by the housing.

11. The buttress applicator of claim 1, further comprising a second buttress assembly, wherein the first buttress assembly is positioned on a first side of the platform, wherein the second buttress assembly is positioned on a second side of the platform.

12. The buttress applicator of claim 11, wherein the lockout feature is adjacent to the second buttress assembly.

13. The buttress applicator of claim 1, wherein the first buttress assembly comprises:
(i) a first longitudinally extending portion, and
(ii) a second longitudinally extending portion, wherein the second longitudinally extending portion is laterally spaced apart from the first longitudinally extending portion.

14. The buttress applicator of claim 13, wherein the second longitudinally extending portion is laterally spaced apart from the first longitudinally extending portion by a distance configured to correspond to a width of a gap defined by a channel formed in an end effector in a surgical stapler.

15. The buttress applicator of claim 1, further comprising a desiccant material disposed on or in the housing.

16. The buttress applicator of claim 15, wherein the desiccant material is configured to change color in response to the presence of moisture.

17. The buttress applicator of claim 16, wherein the housing defines a window, wherein the desiccant material is viewable through the window.

18. The buttress applicator of claim 1, further comprising a cover removably coupled with the housing, wherein the cover is configured to selectively cover the gap defined by the housing.

19. A standalone buttress applicator, configured to apply a buttress material to an end effector of a surgical stapler comprising:

(a) a housing defining a fixed gap configured to receive a portion of an end effector of a surgical stapler;

(b) a platform, wherein a portion of the platform is exposed in the gap defined by the housing and is configured to receive a buttress assembly; and (c) a lockout feature protruding outwardly from the platform, wherein the lockout feature is configured to enable an end effector with an unspent staple cartridge to clamp onto the platform and thereby engage the buttress assembly, wherein the lockout feature is further configured to prevent an end effector with a spent staple cartridge from clamping onto the platform to thereby engage the buttress assembly.

20. A standalone buttress applicator, configured to apply a buttress material to an end effector of a surgical stapler comprising:

(a) a housing defining a fixed gap configured to receive a portion of an end effector of a surgical stapler;

(b) a platform, wherein a portion of the platform is exposed in the gap defined by the housing;

(c) a buttress assembly positioned on the platform, wherein the buttress assembly is exposed in the gap defined by the housing; and (d) a projection extending outwardly from the platform, wherein the projection is configured to be inserted into an elongate channel of a unspent staple cartridge to enable an end effector with the unspent staple cartridge to clamp onto the platform and thereby engage the buttress assembly, wherein the projection is configured to prevent an end effector with a spent staple cartridge from clamping onto the platform to thereby engage the buttress assembly.

* * * * *

UNITED STATES PATENT AND TRADEMARK OFFICE
CERTIFICATE OF CORRECTION

| | | |
|---|---|---|
| PATENT NO. | : 11,039,832 B2 | Page 1 of 1 |
| APPLICATION NO. | : 14/926322 | |
| DATED | : June 22, 2021 | |
| INVENTOR(S) | : Vendely et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1167 days.

Signed and Sealed this
Thirteenth Day of December, 2022

*Katherine Kelly Vidal*

Katherine Kelly Vidal
*Director of the United States Patent and Trademark Office*